United States Patent [19]
Mase et al.

[11] Patent Number: 5,568,865
[45] Date of Patent: Oct. 29, 1996

[54] SURGICAL CABLE PACKAGING APPARATUS

[75] Inventors: Joseph C. Mase, Warsaw, Ind.; Douglas E. Foos, Barrington, Ill.

[73] Assignee: DePuy Inc., Warsaw, Ind.

[21] Appl. No.: 281,823

[22] Filed: Jul. 28, 1994

[51] Int. Cl.⁶ ............................................. A61B 17/06
[52] U.S. Cl. ....................... 206/438; 206/388; 206/363; 206/564
[58] Field of Search .................... 206/63.3, 438, 206/303, 388, 364, 564, 363

[56] References Cited

U.S. PATENT DOCUMENTS

| | | | |
|---|---|---|---|
| 3,972,418 | 8/1976 | Schuler et al. | 206/63.3 |
| 4,084,692 | 4/1978 | Bilweis | 206/63.3 |
| 4,846,343 | 7/1989 | Rupert | 220/555 |
| 5,031,775 | 7/1991 | Kane | 206/438 |
| 5,156,267 | 10/1992 | Yates, Jr. et al. | 206/364 |
| 5,201,495 | 4/1993 | Crates et al. | 220/553 |
| 5,228,565 | 7/1993 | Sinn | 206/63.3 |
| 5,246,104 | 9/1993 | Brown et al. | 206/63.3 |
| 5,263,585 | 11/1993 | Lawhon et al. | 206/388 |
| 5,284,240 | 2/1994 | Alpern et al. | 206/63.3 |

Primary Examiner—David T. Fidei
Attorney, Agent, or Firm—Barnes & Thornburg

[57] ABSTRACT

A tray is provided for storing a surgical cable. The tray includes a body portion configured to define a track for receiving the cable, and a lead-in channel configured to guide the cable into the track. The body portion includes a generally circular recessed portion configured to define an annular track extending around an outer periphery of the recessed portion. The lead-in channel is curved so that the cable enters the annular track in a direction generally tangential to the track. The body portion includes a flange configured to be coupled to a cover for sealing the body portion.

19 Claims, 2 Drawing Sheets

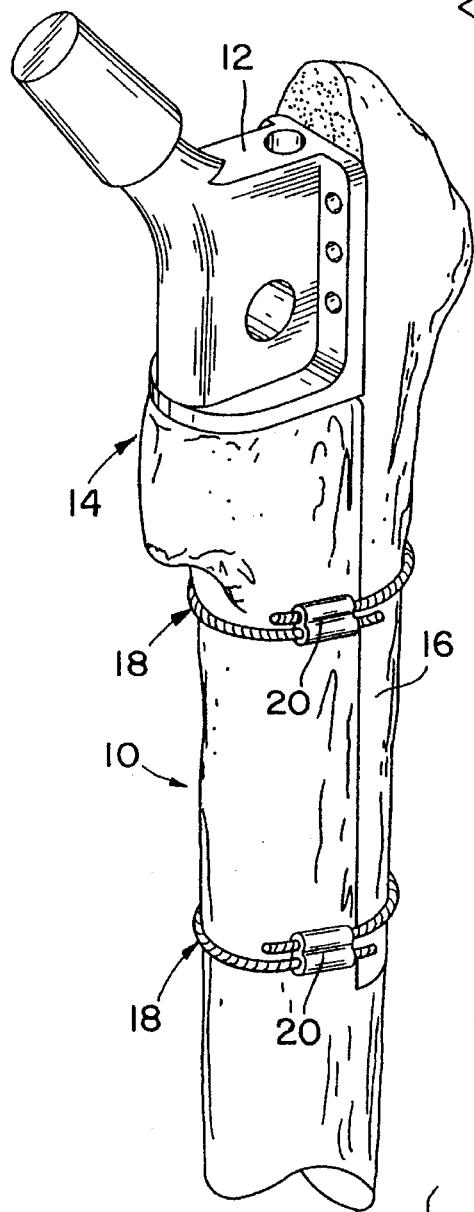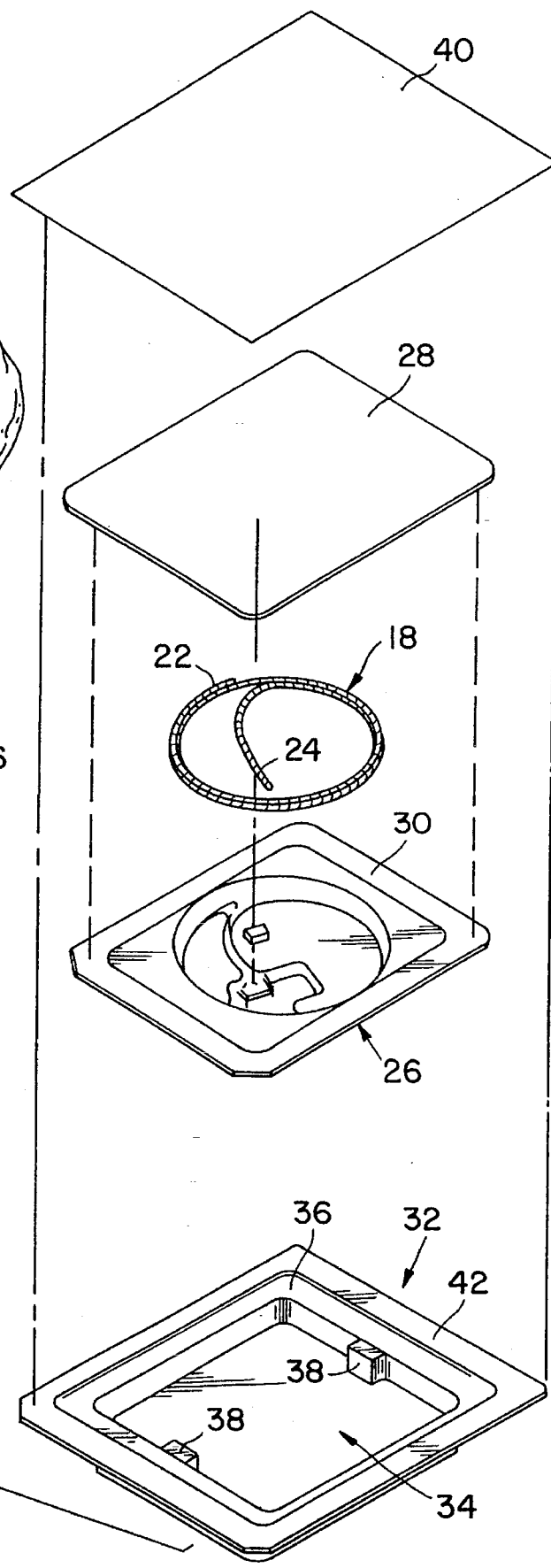
FIG. 1
FIG. 2

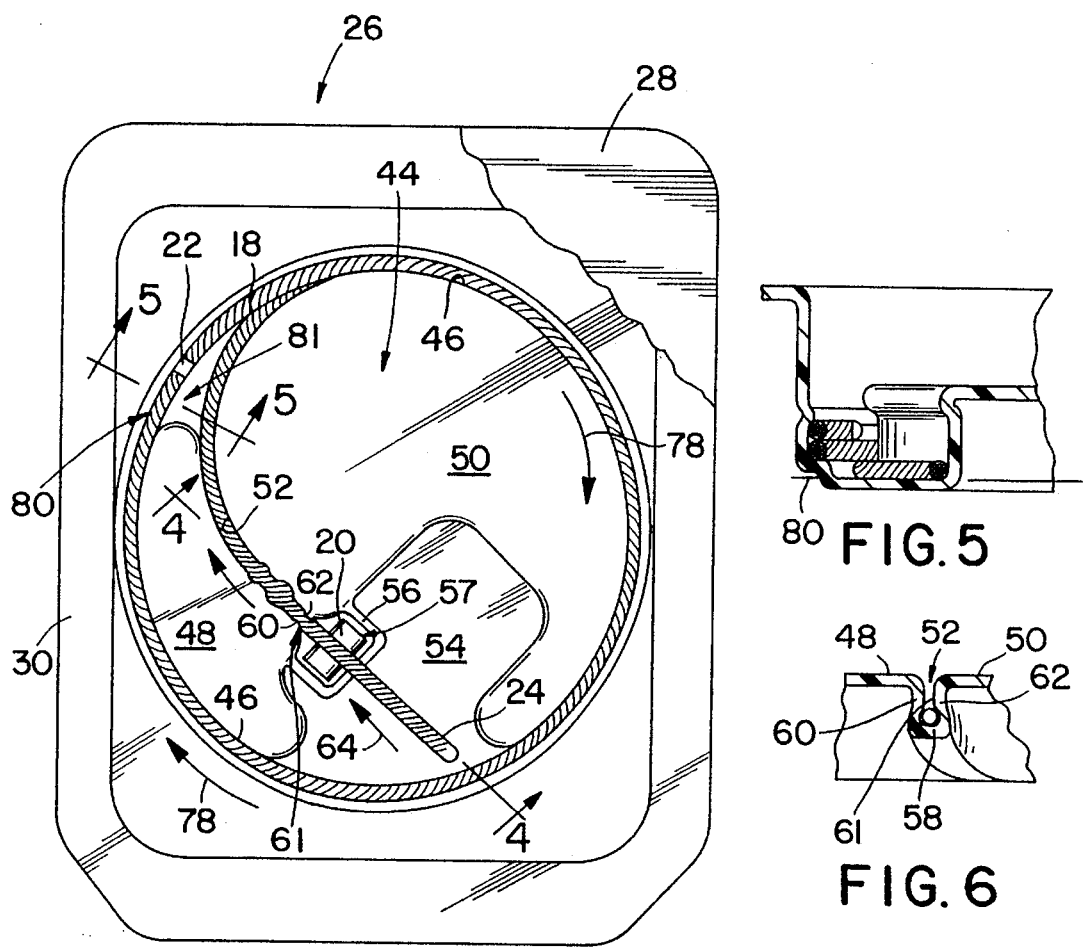

SURGICAL CABLE PACKAGING APPARATUS

BACKGROUND AND SUMMARY OF THE INVENTION

The present invention relates to a packaging apparatus for holding a surgical cable. More particularly, the present invention relates to a packaging tray configured to facilitate storage and use of the surgical cable, while providing a sterile environment for storing the surgical cable prior to use.

It is well known to use a surgical cable in various types of surgical procedures, such as revision hip and knee arthroplasty or trauma fixation. Several preoperative conditions lend themselves to the use of such surgical cables. For example, cable is used in reattachment of extended proximal femoral osteotomy fragments, or in revision hip and knee arthroplasty requiring fixation of strut graphs, fixation of host/graph junctions, or fixation of iatrogenic fractures. Surgical cable is also used for prophylactic cabling of a proximal end of a femur during total hip arthroplasty. In addition, cable is used to repair trauma fractures or for reattachment of trochanter after a trochanteric osteotomy.

One known surgical cable system is a CONTROL™ CABLE SYSTEM available from DePuy Inc. in Warsaw, Ind. The cable is illustratively made from a cobalt chrome alloy having a diameter of about 1.8 mm (0.071 inch) and a length of about 24 inches (60.96 cm). A 7×7 strand configuration is illustratively provided. Opposite ends of the cable are coupled together by a cable sleeve made from a cobalt chrome alloy. The cable sleeve has two apertures extending through a body portion thereof for receiving opposite ends of the cable therethrough. Preferably, the cable sleeve has a low profile design, chamfered entrance holes, and a trapezoidal cross section. An illustrative surgical procedure using a surgical cable is described in a brochure entitled "Control™ Cable—Hip Arthroplasty" from DePuy Inc. in Warsaw, Ind.

The present invention is designed to provide an improved packaging tray for storing a surgical cable and a cable sleeve prior to a surgical procedure. Previous storage techniques involve winding the surgical cable into a coil and then inserting the coiled cable into a medical peel pouch or open cavity thermal formed blister. The plastic pouch is then sealed to keep the cable sterile. A problem associated with storing the surgical cable in a plastic pouch is that the cable tends to unwind wildly or kink when removed from the pouch. In addition, a cable sleeve for use with the cable must be either stored separately or put loosely into the sealed pouch. Therefore, during a surgical procedure, use of the cable is complicated due to the problems associated with storing and removing the sterile coiled cable from a sealed pouch.

The present invention provides a packing apparatus configured to facilitate storage and use of the surgical cable and cable sleeve. In addition, the packaging apparatus provides a sterile barrier to the product before surgery. The packaging apparatus of the present invention advantageously facilitates access to a free end portion of the cable. This facilitates the surgical procedure by making the surgical cable easier to handle in an operating room. The cable is removed from the packaging apparatus of the present invention without unwinding wildly or kinking. The packaging apparatus of the present invention also advantageously stores the cable sleeve in a predetermined portion of the packaging apparatus. This reduces the likelihood that the cable sleeve will be dropped or lost during opening of the packaging apparatus. Advantageously, since the cable and sleeve are packaged together, the packaging apparatus reduces hospital inventory, improves handling in the operating room, and minimizes packaging waste.

According to one aspect of the invention, a tray is provided for storing a surgical cable. The tray includes a body portion configured to define a track for receiving the cable, and a lead-in channel configured to guide the cable into the track.

In the illustrated embodiment, the body portion includes a generally circular recessed portion configured to define an annular track extending around an outer periphery of the recessed portion. The lead-in channel is curved so that the cable enters the annular track in a direction generally tangential to the track.

The annular track includes a ramp portion located adjacent an outlet of the lead-in channel for elevating the cable as the cable passes over the ramp. The lead-in channel also includes a ramp surface for aligning a free end of the cable at an upwardly extending angle.

The lead-in channel is formed to include means for holding the cable within the channel. Illustratively, the lead-in channel is formed by first and second raised surfaces, and the holding means includes first and second projections extending away from the first and second raised surfaces, respectively.

The body portion of the tray includes a wall configured to define a cavity sized to receive a cable sleeve. The wall is located adjacent the lead-in channel so that a free end of the cable extends over the cavity to hold the cable sleeve within the cavity. A recessed portion located adjacent lead-in channel to facilitate access to the free end of the cable.

According to another aspect of the invention, a packaging apparatus includes a first cover configured to be sealed to a flange of the tray. The apparatus also includes an outer tray having an interior region for receiving the sealed inner tray therein and a flange surrounding the interior region. A second cover sealed to the flange of the outer tray.

Additional objects, features, and advantages of the invention will become apparent to those skilled in the art upon consideration of the following detailed description of the preferred embodiment exemplifying the best mode of carrying out the invention as presently perceived.

BRIEF DESCRIPTION OF THE DRAWINGS

The detailed description particularly refers to the accompanying figures in which:

FIG. 1 is a perspective view illustrating a postoperative example of an extended proximal femoral osteotomy fragment reattached to a host bone using a pair of surgical cables;

FIG. 2 is an exploded perspective view illustrating the packaging apparatus of the present invention for storing the surgical cable prior to a surgical procedure;

FIG. 3 is a top plan view illustrating details of an inner storage tray for holding the surgical cable and cable sleeve therein;

FIG. 4 is a sectional view taken along lines 4—4 of FIG. 3 illustrating the position of a free end of the surgical cable within the inner tray and illustrating the position of the cable sleeve which is held in a compartment formed in the inner packaging tray by the free end of the cable;

FIG. 5 is a sectional view taken along lines 5—5 of FIG. 3 illustrating the surgical cable stored in a slot or track formed around the outer periphery of the inner tray and illustrating a ramp formed along a bottom surface of the track to facilitate insertion of the cable into the storage track; and FIG. 6 is a sectional view taken along lines 6—6 of FIG. 4 illustrating the configuration of a lead-in guide channel for guiding insertion of the cable into the track in the inner tray.

DETAILED DESCRIPTION OF THE DRAWINGS

Referring now to the drawings, FIG. 1 illustrates an example of the use of surgical cables in a surgical procedure. In the example of FIG. 1, a host bone 10 is illustratively a femur having an orthopaedic implant 12 installed in a proximal end portion 14. Host bone 10 includes a osteotomy fragment 16 which must be reattached to host bone 10. Therefore, surgical cables 18 are used to hold fragment 16 to bone 10. Cables 18 are first wrapped around bone 10 and fragment 16 using an appropriate cable passer insert. The two free ends of the cable 18 are then passed through opposite ends of a cable sleeve 20. A tensioner is then applied to the cable to apply a predetermined tension force to the cable around the bone 10 and fragment 16. Once an appropriate amount of tension is applied to cables 18, a crimper device is placed around the cable sleeve 20 to crimp sleeve 20 so that sleeve 20 holds cable 18 in proper tension. A cable cutter is then used to cut the free ends of the cable as flush as possible to cable sleeve 20.

The present invention provides an improved packaging apparatus for storing the cable 18 and cable sleeve 20 prior to a surgical procedure. The packaging apparatus is illustrated in FIGS. 2-6. Illustratively, cable 18 includes a first or leading end 22 and a second free end 24. The packaging apparatus of the present invention includes an inner tray 26 illustratively formed by thermal forming a sheet of plastic resin, illustratively in a plug assisted vacuum environment. It will be appreciated that various types of forming processes may be used to form tray 26. Tray 26 may preferably be formed from Polyethylene Terephthalate with a glycol modifier(PETG). Tray 26 has a length of about 5.0 inches (12.7 cm) and a width of about 4.25 inches (10.8 cm). A sheet 28 of heat seal coated high density polyethylene (HDPE) is then sealed to an outer flange 30 of inner tray 26 in a conventional manner after a sterile cable 18 and sleeve 22 are loaded into tray 26 as discussed below. The packaging apparatus of the present invention also includes an outer tray 32 for receiving sealed inner tray 26. Outer tray 32 includes an interior region 34 for receiving inner tray 26. A recessed portion 36 is configured to receive flange 30 of inner tray 26. Positioning lugs 38 are formed on opposite end portions of interior region 34. Another sheet 40 of high density polyethylene is sealed to flange 42 of outer tray 32 after inner tray 26 is loaded into interior region 34. Outer flange 42 has a length of about 6.25 inches (15.88 cm) and a width of about 5.25 inches (13.34 cm). Recessed portion 36 has a length of about 5.115 inches (12.99 cm) and a width of about 4.39 inches (11.15 cm).

As illustrated in FIG. 3, inner tray 26 includes a recessed, generally circular cable storage portion 44 extending below flange 30. Storage portion 44 is configured to define a generally annular track portion 46 extending around an outer periphery of circular storage portion 44 for holding surgical cable 18 therein. Circular storage portion 44 has a diameter of about 3.5 inches (8.9 cm). Storage portion 44 includes first and second spaced apart raised sections 48 and 50 defining a lead-in channel 52 therebetween, and an open or recessed portion 54 located below raised portions 48 and 50. Recessed portion 54 is configured to lie adjacent free end 24 of cable 18 to facilitate access to free end 24. A retaining wall 56 is formed within recessed portion 54. Wall 56 defines a cavity 57 sized for holding a cable sleeve 20 therein. Circular storage portion 44 is formed to extend about 0.56 inch (1.42 cm) below flange 30 as illustrated by dimension 59 in FIG. 4.

FIG. 4 illustrates a lead-in guide channel 52. Lead-in channel 52 includes a ramp portion 58 aligned at an angle relative to bottom surface of circular portion 44 and relative to a plane of flange 30 of inner tray 26. A pinch point 61 is formed by projections 60 and 62 located above lead-in ramp 58 on raised sections 48 and 50 as illustrated in FIGS. 3 and 6. Illustratively, pinch point 61 has a dimension between projections 60 and 62 which is less than the diameter of cable 18 so that cable 18 will not move out of lead-in guide track 52. In other words, projections 60 and 62 provide means for holding cable 18 within lead-in channel 52. Illustratively, the dimension between projections 60 and 62 is about 0.060 inch (1.524 mm). The diameter of cable 18 is about 1.8 mm (0.071 inch).

As illustrated in FIG. 3, lead-in channel 52 is curved so that as first end 22 of cable 18 is inserted into lead-in channel 52 in the direction of arrow 64 in FIGS. 3 and 4, the curved channel 52 bends the cable 18 so that end 22 approaches track 46 generally tangential to the annular track 46 formed along the outer periphery of circular portion 44. This curved lead-in channel 52 facilitates insertion of cable 18 into track 46. Preferably, track 46 is crimped along a top portion thereof to reduce the likelihood that cable 18 will be removed through the top of open track 46. This is illustrated in FIG. 4. An annular indented portion 66 is formed around an outer periphery of circular portion 44 to prevent cable 18 from escaping through the open top portion of track 46. Track 46 has a height dimension 45 of about 0.150 inch (3.81 mm) and a width dimension 47 of about 0.1 inch (2.54 mm). The open top of track 46 has a dimension of about 0.050 inch (1.27 mm).

FIG. 4 also illustrates cable sleeve 20 having apertures 68 and 70 formed therein for receiving first and second ends 22 and 24, respectively, of cable 18. Cavity 57 is formed adjacent the entry portion 72 of lead-in channel 52. Therefore, a portion of cable 18, held down by projections 60 and 62, holds cable sleeve 20 within cavity 57. In other words, free end 24 of cable 18 provides a spring force against cable sleeve 20 in the direction of arrow 74 to retain cable sleeve 20 within cavity 57. Free end 24 of cable 18 is aligned at an upperly extending angle relative to a plane of flange 30 to facilitate access to the free end 24 of cable 18 by a surgeon in the operating room. FIG. 4 illustrates a finger 76 located within recessed portion 54 for easy gripping free end 24 of cable 18.

During insertion, a passive cable sleeve 20 is first loaded into cavity 57 in a clean room environment. A passive cable 18 is then loaded into inner tray 26. A leading first end 22 of cable 18 is inserted into lead-in channel 52 below projections 60 and 62 in the direction of arrow 64. Cable 18 is pushed into track 46 so that the cable 18 winds itself in track 46 in the direction of arrows 78 in FIG. 3. Tray 26 is a form to include a ramp portion 80 located adjacent an outlet 81 of lead-in channel 52. Therefore, as leading end 22 of cable 18 approaches one full loop inside track 46, ramp 80 elevates the leading end 22 of cable 18 so that leading end 22 passes over the portion of cable 18 already in track 46.

By moving the leading end 22 of cable 18 above the top of the cable 18 already inserted into the track 46, continued smooth insertion of the cable 18 into track 46 is facilitated. FIG. 5 illustrates this layered cable and ramp feature. After the sterile cable 18 is loaded into tray 26 with a free end 24 situated over recessed portion 54 for easy access and for holding cable sleeve 20 in place within cavity 57, cover sheet 28 is secured to flange 30 of inner tray 26 in a conventional manner. Sealed inner tray 26 is in placed in outer tray 32, and cover sheet 40 is sealed to flange 42 of outer tray 32. The entire sealed package is then sterilized using gamma radiation which penetrates the sealed surfaces without breaking the seals between cover sheet 28 and flange 30 or cover sheet 40 and flange 42. Therefore, the sealed inner tray 26 with product remains sterilized while the packaging apparatus is shipped or stored. The outer surface of the outer tray 32 and cover 40 may become contaminated during storage. However, during a surgical procedure, the sterile inner tray 26 is removed and taken into the sterile operating field. Advantageously, the cable 18 and cable sleeve 20 are packaged together. This reduces hospital inventory and minimizes packaging waste. The improved design for inner tray 26 also facilitates handling of cable 18 and cable sleeve 20 in the operating room.

Although the invention has been described in detail with reference to a certain preferred embodiment, variations and modifications exist within the scope and spirit of the present invention as described and defined in the following claims.

What is claimed is:

1. A tray for storing a surgical cable, the tray comprising:
   a body portion configured to define a track for receiving the cable; and
   a lead-in channel configured to guide the cable into the track, the lead-in channel being formed to include means for holding the cable within the channel.

2. The tray of claim 1, wherein the lead-in channel is formed by first and second raised surfaces, and the holding means includes first and second projections extending away from the first and second raised surfaces, respectively.

3. The tray of claim 1, further comprising a recessed portion located adjacent lead-in channel to facilitate access to the free end of the cable.

4. The tray of claim 1, further comprising a wall configured to define a cavity sized to receive a cable sleeve therein, the wall being located adjacent the lead-in channel so that a free end of the cable extends over the cavity to hold the cable sleeve within the cavity.

5. The tray of claim 1, wherein the body portion includes a flange configured to be coupled to a cover for sealing the body portion.

6. The tray of claim 1, wherein the body portion includes a generally circular recessed portion configured to define an annular track extending around an outer periphery of the recessed portion.

7. The tray of claim 2, wherein the lead-in channel is curved so that the cable enters the annular track in a direction generally tangential to the track.

8. The tray of claim 3, wherein the annular track includes a ramp portion located adjacent an outlet of the lead-in channel for elevating the cable as the cable passes over the ramp.

9. The tray of claim 1, wherein the lead-in channel includes a ramp surface for aligning a free end of the cable at an upwardly extending angle.

10. A packaging apparatus for storing a surgical cable, the packaging apparatus comprising:
    an inner tray having a body portion configured to define a track for receiving the cable, and a flange surrounding the track;
    a first cover sealed to the flange of the inner tray;
    an outer tray having an interior region for receiving the sealed inner tray therein and a flange surrounding the interior region; and
    a second cover sealed to the flange of the outer tray.

11. The apparatus of claim 10, wherein the body portion of the inner tray includes a generally circular recessed portion configured to define an annular track extending around an outer periphery of the recessed portion.

12. The apparatus of claim 11, wherein the body portion of the inner tray is formed to include a lead-in channel for guiding the cable into the annular track, the lead-in channel being curved so that the cable enters the annular track in a direction generally tangential to the track.

13. The apparatus of claim 12, wherein the inner tray includes a wall configured to define a cavity sized to receive a cable sleeve therein, the wall being located adjacent the lead-in channel so that a free end of the cable extends over the cavity to hold the cable sleeve within the cavity.

14. The apparatus of claim 13, wherein the inner tray is formed to include a recessed portion located adjacent lead-in channel to facilitate access to the free end of the cable.

15. A tray for storing a surgical cable, the tray comprising:
    a body portion configured to define a track for receiving the cable;
    means for guiding the cable into the track during insertion of the cable into the track; and
    a wall configured to define a cavity sized to receive a cable sleeve therein, the wall being located adjacent the track, and means for holding a free end of the cable in a position extending over the cavity to retain the cable sleeve within the cavity.

16. The tray of claim 15, wherein the body portion includes a generally circular recessed portion configured to define an annular track extending around an outer periphery of the circular recessed portion.

17. The tray of claim 16, wherein the guiding means includes a curved lead-in channel configured so that the cable enters the annular track in a direction generally tangential to the track.

18. The tray of claim 15, further comprising a recessed portion located adjacent the cavity to facilitate access to the free end of the cable.

19. The tray of claim 1, wherein the annular track includes a circumference and the lead-in channel is situated within the circumference.

* * * * *